United States Patent
Lee et al.

(10) Patent No.: US 8,658,183 B2
(45) Date of Patent: Feb. 25, 2014

(54) ANTIMICROBIAL PARENTERAL FORMULATION

(75) Inventors: Lih-Huei Lee, Taipei (CN); Po-Yi Wu, Banciao (CN); Erkuan Sun, Jiangsu (CN); Chi-Hsin Richard King, Holladay, UT (US)

(73) Assignee: Taigen Biotechnology Company, Ltd., Taipei (TW)

( * ) Notice: Subject to any disclaimer, the term of this patent is extended or adjusted under 35 U.S.C. 154(b) by 1358 days.

(21) Appl. No.: 11/836,241

(22) Filed: Aug. 9, 2007

(65) Prior Publication Data

US 2009/0042932 A1 Feb. 12, 2009

(51) Int. Cl.
*A61K 9/00* (2006.01)
*A61K 31/47* (2006.01)
*A61K 47/12* (2006.01)
*A61K 31/4725* (2006.01)

(52) U.S. Cl.
CPC ............. *A61K 9/0019* (2013.01); *A61K 9/0012* (2013.01); *A61K 47/12* (2013.01); *A61K 31/4725* (2013.01)
USPC ........................... 424/400; 514/312; 514/314

(58) Field of Classification Search
USPC .................. 514/312, 314; 424/400
See application file for complete search history.

(56) References Cited

U.S. PATENT DOCUMENTS

| | | |
|---|---|---|
| 6,329,391 B1 | 12/2001 | Ledoussal et al. |
| 2004/0038975 A1 | 2/2004 | Ledoussal et al. |
| 2005/0065164 A1* | 3/2005 | De Souza et al. ........ 514/253.08 |
| 2007/0232650 A1* | 10/2007 | Redman-Furey et al. .... 514/312 |

FOREIGN PATENT DOCUMENTS

| | | |
|---|---|---|
| WO | WO99/14214 | 3/1999 |
| WO | WO99/35117 | 7/1999 |
| WO | WO02/48113 | 6/2002 |
| WO | WO2004/013103 | 2/2004 |
| WO | WO2007/110834 | 10/2007 |
| WO | WO2007/110835 | 10/2007 |
| WO | WO2007/110836 | 10/2007 |

OTHER PUBLICATIONS

Ansel et al. Pharmaceutical dosage forms and drug delivery systems, Sixth edition, Williams & Wilkins, 1995, pp. 398-401.*
"TaiGen Initiates Phase II Trial of Nemonoxacin for Treatment of Adult Community Acquired Pneumonia (CAP)", Jan. 8, 2007, retrieved from Internet May 14, 2008, 2 pages.

* cited by examiner

*Primary Examiner* — Shengjun Wang
(74) *Attorney, Agent, or Firm* — Cesari and McKenna, LLP

(57) ABSTRACT

This invention relates to a parenteral formulation containing an effective amount of the compound of the following formula I:

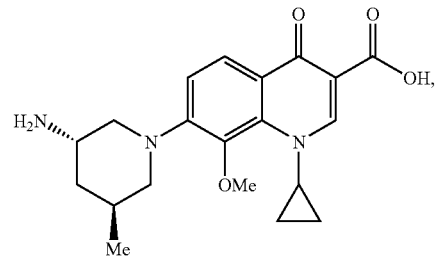

Formula I water, and an isotonic agent. Also disclosed is a method of treating an infectious disease by administering this formula to a subject via parenteral injection or infusion.

27 Claims, No Drawings

ANTIMICROBIAL PARENTERAL FORMULATION

BACKGROUND OF THE INVENTION

Parenteral injection of an antimicrobial drug is one of the most effective ways to treat infections, especially those with methicillin-resistant *Staphylococcus aureus* and multi-resistant *Streptococcus pneumoniae*. It requires use of an aqueous formulation that is a stable solution.

SUMMARY

In one aspect, this invention features an antimicrobial parenteral formulation (e.g., intravenous formulation), which contains a compound of formula I shown below:

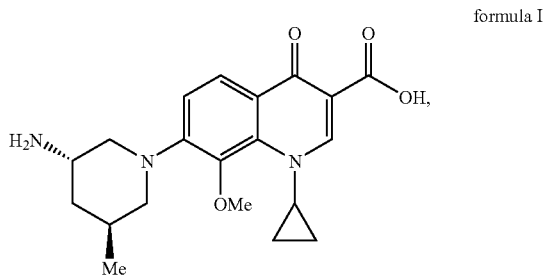

formula I water, and an isotonic agent. The compound and the isotonic agent are dissolved in the water to form a parenteral formulation.

The compound includes its salts and prodrugs. The salts, for example, can be formed between a positively charged amino group on the compound and an anion. Suitable anions include, but are not limited to, chloride, bromide, iodide, sulfate, nitrate, phosphate, D- or L-malate, D,L-malate, citrate, tosylate, mesylate, D- or L-tartrate, D,L-tratrate, fumarate, trifluoroacetate, L-glutamate, D-glucuronate, maleate, lactate, and acetate. Likewise, a negatively charged carboxylate on the compound can form a salt with a cation. Suitable cations include, but are not limited to, sodium ion, potassium ion, magnesium ion, calcium ion, and an ammonium cation such as tetramethylammonium ion. Examples of prodrugs include esters and other pharmaceutically acceptable derivatives, which, upon administration to a subject, are capable of providing the compound described above (see Goodman and Gilman's, The Pharmacological basis of Therapeutics, $8^{th}$ ed., McGraw-Hill, Int. Ed. 1992, "Biotransformation of Drugs"). In addition, the compound, having asymmetric centers, can occur as racemates, racemic mixtures, single enantiomers, individual diastereomers, and diastereomeric mixtures.

An isotonic agent, such as nonelectrolytes and electrolytes, adjusts an osmotic pressure ratio. See U.S. Pat. No. 6,015,810. Examples include, but are not limited to, glycerine, lactose, mannitol, dextrose, sodium chloride, sodium sulfate, and sorbitol.

In the formulation of this invention, the compound may have a concentration of 0.2 to 45 mM, and the isotonic agent may have a concentration of 0.2% to 13% w/v, particularly, 0.2% to 1.3% w/v.

The concentration of the isotonic agent ("% w/v") is calculated as the ratio between the weight (g) of the isotonic agent and the volume (liter) of the formulation.

The formulation of this invention may further contain a buffer, a stabilizing agent, or an antioxidant.

An example for the formulation of this invention is one containing malate salt of the compound at the concentration of 0.2 to 45 mM, sodium chloride at the concentration of 0.9% w/v, a stabilizing agent at a concentration of 0.1-1.0% w/v, and a buffer at a concentration of 0.01-5% w/v. As another example, the formulation contains malate salt of the compound 0.2 to 45 mM, dextrose at the concentration of 1-7% w/v, a stabilizing agent at a concentration of 0.1-1.0% w/v, and a buffer at a concentration of 0.01-5% w/v.

Like that of the isotonic agent, the concentrations of the stabilizing agent, the buffer, and the antioxidant are also calculated as the ratio between the weight of the reagent and the volume of the formulation.

In another aspect, this invention features a method of treating an infectious disease by administering via parenteral injection to a subject an effective amount of the above-described formulation. The infectious disease may be caused by infection with Gram positive bacteria, Gram negative bacteria, anaerobic bacteria, methicillin-resistant *S. aureus*, or multi-resistant *S. pneumoniae*. Examples of the infectious disease include, but are not limited to, urinary tract infection, prostatitis, respiratory infection, osteomyelitis, gonorrhea, *mycobacterium tuberculosis*, *mycobacterium avium* complex, acute exacerbations of chronic bronchitis, pneumonias, sinusitis, infectious diarrhea, *helicobacter pylori*, skin infection, gynecologic infection, and abdominal infection.

Also within the scope of this invention is use of the above-described formulation via parenteral injection to treat an infectious disease.

The details of one or more embodiments of the invention are set forth in the description below. Other features, objects, and advantages of the invention will be apparent from the description and from the claims.

DETAILED DESCRIPTION OF THE INVENTION

The compound of formula I used to practice this invention can be synthesized by conventional methods. See Example 1 below.

The compound thus synthesized can be further purified by flash column chromatography, high performance liquid chromatography, crystallization, or any other suitable methods.

To prepare the parenteral formulation of this invention, one can simply mix the compound of formula I, an isotonic agent, and water at the desired ratio in any sequence. For example, one can mix a predetermined amount of the compound with saline (an aqueous solution containing sodium chloride, an isotonic agent) at a predetermined concentration. Mixing can be achieved by shaking, agitation, or swirling and is controlled to reconstitute the solid ingredient(s) into water without causing severe foaming. At any stage of the preparation, sterilization, e.g., an autoclave, may be applied.

The formulation of this invention may further contain one or more additives, such as a buffer, a stabilizing agent, and an antioxidant. Examples of a buffer include, but are not limited to, acetate, citrate, tartarate, lactate, succinate, malate, and phosphate. Examples of stabilizing agent include, but are not limited to, histidine, lysine, glycine, sucrose, fructose, trehalose, and a mixture thereof. Examples of an antioxidant include, but are not limited to, sodium bisulfite, butylated hydroxy anisole, cysteine, gentisic acid, monosodium glutamate, sodium thioglycolate, and ascorbic acid.

The additives can be included in the formulation at any stage of its preparation. The suitable concentration of an additive in the formulation for conferring the intended effect, as recognized by those skilled in the art, can be assayed using conventional methods.

The formulation of this invention can be used immediately after the preparation or can be stored for later use. For immediate use, a kit having a vial containing the compound of formula I and another vial containing an isotonic agent or an aqueous solution containing an isotonic agent can be provided. Alternatively, a kit having a vial containing the compound of formula I and another vial containing a water solution of an isotonic agent (e.g., saline) can be provided. The kit may also contain one or more additives, such as a stabilizing agent, a buffer, or an antioxidant. Shortly prior to administration, one can mix the substances provided in the kit to prepare the formulation.

One can employ the formulation of this invention to treat infectious disease by administering via parenteral injection or infusion to a subject in need of the treatment an effective amount of the formulation.

As used herein, the term "treating" or "treatment" is defined as the administration of an effective amount of the formulation to a subject, who has an infectious disease, a symptom of the infection, a disease or disorder secondary to the infection, or a predisposition toward the infection, with the purpose to cure, alleviate, relieve, remedy, or ameliorate the infectious disease, the symptom of the infection, the disease or disorder secondary to the infection, or the predisposition toward the infection.

The term "an effective amount" refers to an amount of the formulation which confers a therapeutic effect on the treated subject.

The term "parenteral" as used herein includes subcutaneous, intracutaneous, intravenous, intramuscular, intraarticular, intraarterial, intrasynovial, intrasternal, intrathecal, intralesional, and intracranial injection or infusion techniques. Among them, intravenous injection or infusion is preferred.

Without further elaboration, it is believed that the above description has adequately enabled the present invention. The following examples are, therefore, to be construed as merely illustrative, and not limitative of the remainder of the disclosure in any way whatsoever. All of the publications cited herein are hereby incorporated by reference in their entirety.

EXAMPLE 1

Malate salt of (3S,5S)-7-[3-amino-5-methyl-piperidinyl]-1-cyclopropyl-1,4-dihydro-8-methoxy-4-oxo-3-quinolinecarboxylic acid (Compound 1) was synthesized as follows:

(A) Synthesis of (3S,5S)-(5-Methyl-piperidin-3-yl)-carbamic acid tert-butyl ester (Compound 9)

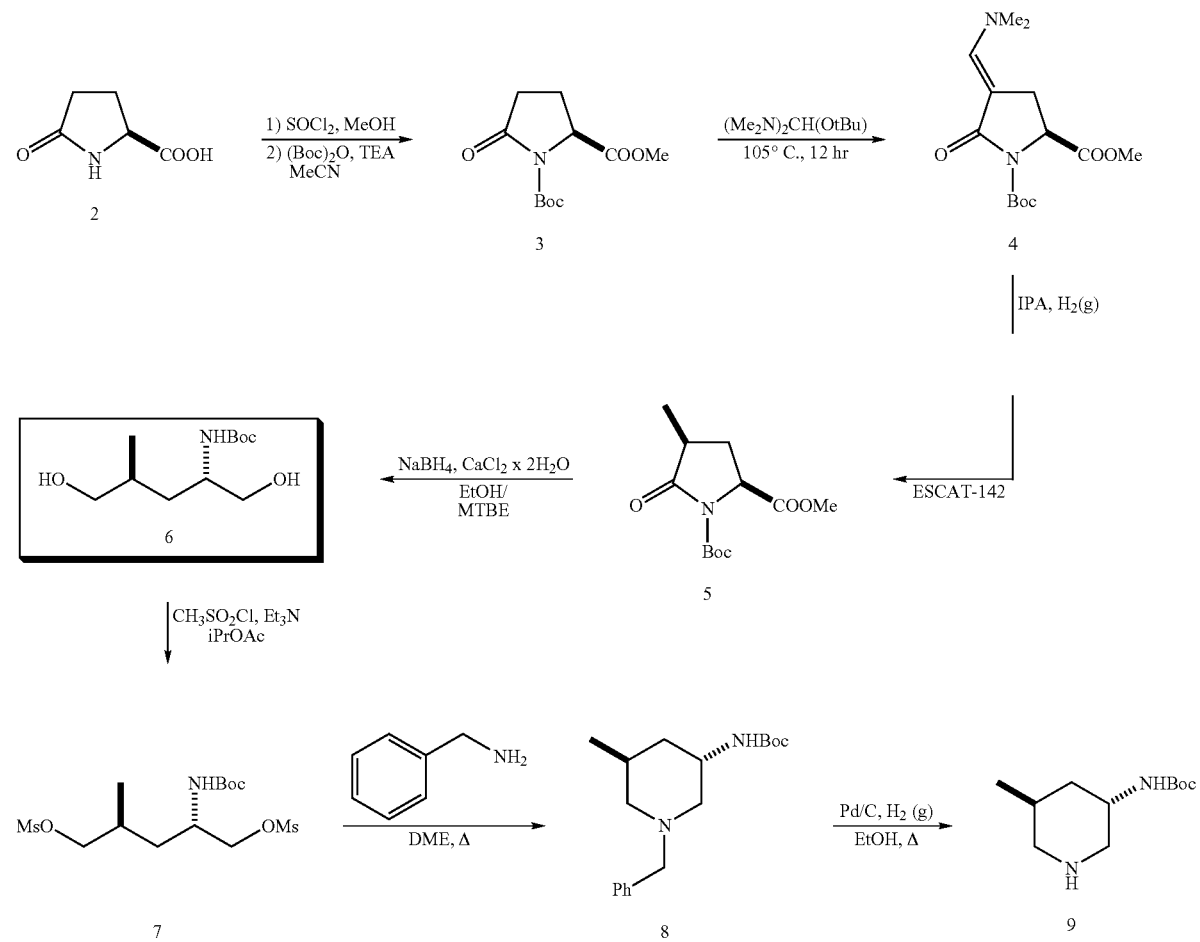

Scheme 1

A 50-L reactor was charged with Compound 2 (5.50 kg, 42.60 mol), methanol (27 L) and cooled to 10-15° C. Thionyl chloride (10.11 kg, 2.0 equiv.) was added via an addition funnel over a period of 65 min, with external cooling to keep temperature below 30°. The resulting solution was stirred at 25° C. for 1.0 hour, after which methanol was removed under reduced pressure. The oily residue was azeotroped with ethyl acetate (3×2.5 L) to remove residual methanol, dissolved in ethyl acetate (27.4 L), charged into a 50 L reactor, and neutralized by slow addition of triethylamine (3.6 kg) below 30° C. The resulting suspension was filtered to remove triethylamine hydrochloride.

The filtrate was charged to a 50 L reactor, along with DMAP (0.53 kg). Di-tert-butyl dicarbonate (8.43 kg) was added via hot water heated addition funnel, over a period of 30 min at a temperature of 20-30° C. The reaction was complete after 1 hour as determined by TLC analysis. The organic phase was washed with ice cold 1N HCl (2×7.5 L), saturated sodium bicarbonate solution (1×7.5 L), dried over magnesium sulfate, and filtered. After ethyl acetate was removed under reduced pressure, crystalline slurry was obtained, triturated with MTBE (10.0 L), and filtered to afford Compound 3 as a white solid (5.45 kg, 52.4%).

Anal. Calcd for $C_{11}H_{17}NO_5$: C, 54.3; H, 7.04; N, 5.76. Found: C, 54.5; H, 6.96; N, 5.80. HRMS (ESI$^+$) Expected for $C_{11}H_{18}NO_5$, [M+H] 244.1185. Found 244.1174; $^1$H NMR (CDCl$_3$, 500 MHz): =4.54 (dd, J=3.1, 9.5 Hz, 1H), 3.7 (s, 3H), 2.58-2.50 (m, 1H), 2.41 (ddd, 1H, J=17.6, 9.5, 3.7), 2.30-2.23 (m, 1H), 1.98-1.93 (m, 1H), 1.40 (s, 9H); $^{13}$C NMR (CDCl$_3$, 125.70 MHz) δ 173.3, 171.9, 149.2, 83.5, 58.8, 52.5, 31.1, 27.9, 21.5; Mp 70.2° C.

A 50-L reactor was charged with Compound 3 (7.25 kg, 28.8 mol), DME (6.31 kg), and Bredereck's Reagent (7.7 kg, 44.2 mole). The solution was agitated and heated to 75° C.±5° C. for three hours. The reaction was cooled to 0° C. over an hour, during which time a precipitate formed. The mixture was kept at 0° C. for an hour, filtered, and dried in a vacuum oven for at least 30 hours at 30° C.±5° C. to give compound 4 as a white crystalline solid (6.93 kg, 77.9%).

Anal. Calcd for $C_{14}H_{22}N_2O_5$: C, 56.4; H, 7.43; N, 9.39. Found C, 56.4; H, 7.32; N, 9.48. HRMS (ESI$^+$) Expected for $C_{14}H_{22}N_2O_5$, [M+H] 299.1607. Found 299.1613; $^1$H NMR (CDCl$_3$, 499.8 MHz) δ=7.11 (s, 1H), 4.54 (dd, 1H, J=10.8, 3.6), 3.74 (s, 3H), 3.28-3.19 (m, 1H), 3.00 (s, 6H), 2.97-2.85 (m, 1H), 1.48 (s, 9H); $^{13}$C NMR (CDCl$_3$, 125.7 MHz) δ=172.6, 169.5, 150.5, 146.5, 90.8, 82.2, 56.0, 52.3, 42.0, 28.1, 26.3. MP 127.9° C.

A 10-gallon Pfaudler reactor was charged with ESCAT 142 (Engelhard Corp. N.J., US) 5% palladium powder on carbon (50% wet, 0.58 kg wet wt.), Compound 4 (1.89 kg, 6.33 mol), and isopropanol (22.4 Kg). After agitated under a 45-psi hydrogen atmosphere at 45° C. for 18 hrs, the reaction mixture was cooled to room temperature and filtered though a bed of Celite (0.51 kg). The filtrate was evaporated under reduced pressure to give a thick oil, which was solidified on standing to afford Compound 5 (1.69 kg, 100%) as a 93:7 diastereomeric mixture.

A sample of product mixture was purified by preparative HPLC to give material for analytical data. Anal. Calcd for $C_{12}H_{19}NO_5$: C, 56.0; H, 7.44; N, 5.44. Found C, 55.8; H, 7.31; N, 5.44. MS (ESI$^+$) Expected for $C_{12}H_{19}NO_5$, [M+H] 258.1342. Found 258.1321; $^1$H NMR (CDCl$_3$, 499.8 MHz) δ=4.44 (m, 1H), 3.72 (s, 3H), 2.60-2.48 (m, 2H), 1.59-1.54 (m, 1H), 1.43 (s, 9H), 1.20 (d, j=6.8 Hz, 3H); $^{13}$C NMR (CDCl$_3$, 125.7 MHz) δ=175.7, 172.1, 149.5, 83.6, 57.4, 52.5, 37.5, 29.8, 27.9, 16.2. Mp 89.9° C.

A 50-L reactor was charged with Compound 5 (3.02 kg, 11.7 mol), absolute ethanol (8.22 kg), and MTBE (14.81 kg). Sodium borohydride (1.36 kg, 35.9 mol) was added in small portions at 0° C.±5° C. A small amount of effervescence was observed. The reaction mixture was warmed to 10° C.±5° C. and calcium chloride dihydrate (2.65 kg) was added in portions at 10° C.±5° C. over an hour. The reaction was allowed to warm to 20° C.±5° C. over one hour and agitated for an additional 12 hours at 20° C.±5° C. After the reaction was cooled to −5° C.±5° C., ice-cold 2N HCl (26.9 kg) was added slowly at of 0° C.±5° C. Agitation was stopped. The lower aqueous phase was removed. The reactor was charged with aqueous saturated sodium bicarbonate (15.6 kg) over five minutes under agitation. Agitation was stopped again and the lower aqueous phase was removed. The reactor was charged with magnesium sulfate (2.5 kg) and agitated for at least 10 minutes. The mixture was filtered though a nutsche filter, and concentrated under reduced pressure to afford Compound 6 (1.80 kg, 66%).

Anal. Calcd for $C_{11}H_{23}NO_4$: C, 56.6H, 9.94; N, 6.00. Found C, 56.0; H, 9.68; N, 5.96. HRMS (ESI$^+$) Expected for $C_{11}H_{24}NO_4$, [M+H] 234.1705. Found 234.1703; $^1$H NMR (CDCl$_3$, 500 MHz) δ=6.34 (d, J=8.9 Hz, 1H, NH), 4.51 (t, J=5.8, 5.3 Hz, 1H, NHCHCH$_2$OH), 4.34 (t, J=5.3, 5.3 Hz, 1H, CH$_3$CHCH$_2$OH), 3.46-3.45, (m, 1H, NHCH), 3.28 (dd, J=10.6, 5.3 Hz, NHCHCHHOH), 3.21 (dd, J=10.2, 5.8 Hz, 1H, CH$_3$CHCHHOH), 3.16 (dd, J=10.2, 6.2 Hz, 1H, NHCHCHHOH), 3.12 (dd, J=10.6, 7.1 Hz, 1H, CH$_3$CHC HHOH), 1.53-1.50 (m, 1H, CH$_3$CHCHHOH), 1.35 (s, 9H, O(CH$_3$)$_3$), 1.30 (ddd, J=13.9, 10.2, 3.7 Hz, 1H, NHCHCH HCH), 1.14 (ddd, J=13.6, 10.2, 3.4 Hz, 1H, NHCHCHHCH), 0.80 (d, J=6.6 Hz, 3H, CH$_3$); $^{13}$C NMR (CDCl$_3$, 125.7 MHz) δ 156.1, 77.9, 50.8, 65.1, 67.6, 65.1, 35.6, 32.8, 29.0, 17.1. Mp 92.1° C.

A 50 L reactor was charged with a solution of Compound 6 (5.1 kg) in isopropyl acetate (19.7 kg). The reaction was cooled to 15° C.±5° C. and triethylamine (7.8 kg) was added at that temperature. The reactor was further cooled to 0° C.±5° C. and methanesulfonyl chloride (MsCl) (6.6 kg) was added. The reaction was stirred for a few hours and monitored for completion by HPLC or TLC. The reaction was quenched by saturated aqueous bicarbonate solution. The organic phase was isolated and washed successively with cold 10% aqueous triethylamine solution, cold aqueous HCl solution, cold saturated aqueous bicarbonate solution, and finally saturated aqueous brine solution. The organic phase was dried, filtered, and concentrated in vacuo below 55° C.±5° C. to afford compound 7 as a solid/liquid slurry, which was used in the subsequent reaction without further purification.

After charged with 9.1 kg of neat benzylamine, a 50 L reactor was warmed to 55° C., at which temperature, a solution of compound 7 (8.2 kg) in 1,2-dimethoxyethane (14.1 kg) was added. After the addition, the reaction was stirred at 60° C.±5° C. for several hours and monitored for completion by TLC or HPLC. The reaction was cooled to ambient temperature and the solvent was removed under vacuum. The residue was diluted with 11.7 kg of 15% (v/v) ethyl acetate/hexanes solution and treated, while agitating, with 18.7 kg of 20% (wt) aqueous potassium carbonate solution. A triphasic mixture was obtained upon standing. The upper organic layer was collected. The isolated middle layer was extracted twice again with 11.7 kg portions of 15% (v/v) ethyl acetate/hexanes solution. The combined organic layers were concentrated under vacuum to give an oily residue. The residue was then purified by chromatography to afford Compound 8 as an oil.

A 40 L pressure vessel was charged with 0.6 kg 50% wet, solid palladium on carbon (E101, 10 wt. %) under flow of nitrogen. A solution of Compound 8 (3.2 kg) in 13.7 kg of absolute ethanol was then added to the reactor under nitrogen. The reactor was purged with nitrogen and then pressurized with hydrogen at 45 psi. The reaction was then heated to 45° C. It was monitored by TLC or LC. Upon completion, the reaction was cooled to ambient temperature, vented, and purged with nitrogen. The mixture was filtered through a bed of Celite and the solid was washed with 2.8 kg of absolute ethanol. The filtrate was concentrated under vacuum to afford Compound 9 as a waxy solid.

TLC $R_f$ (Silica $F_{254}$, 70:30 v/v ethyl acetate-hexanes, $KMnO_4$ stain)=0.12; $^1$H NMR (300 MHz, $CDCl_3$) δ 5.31 (br s, 1H), 3.80-3.68 (m, 1H), 2.92 (d, J=11.4 Hz, 1H), 2.77 (AB quart, $J_{AB}$=12.0 Hz, v=50.2 Hz, 2H), 2.19 (t, J=10.7 Hz, 1H), 1.82-1.68 (m, 2H), 1.54 (br s, 1H), 1.43 (s, 9H), 1.25-1.15 (m, 1H), 0.83 (d, J=6.6 Hz, 3H); $^{13}$C NMR (75 MHz, $CDCl_3$) δ: 155.3, 78.9, 54.3, 50.8, 45.3, 37.9, 28.4, 27.1, 19.2; MS (ESI$^+$) m/z 215 (M+H), 429 (2M+H).

(B) Synthesis of 1-Cyclopropyl-7-fluoro-8-methoxy-4-oxo-1,4-dihydro-quinoline-3-carboxylic acid (Compound 10)

Compound 10 was prepared according to the method described in U.S. Pat. No. 6,329,391.

(C) Synthesis of borone ester chelate of 1-Cyclopropyl-7-fluoro-8-methoxy-4-oxo-1,4-dihydro-quinoline-3-carboxylic acid (Compound 11)

Scheme 2 a. $CH_3COOH$, $(CH_3CO)_2O$
reflux, 2 h
b. $B_2O_3$

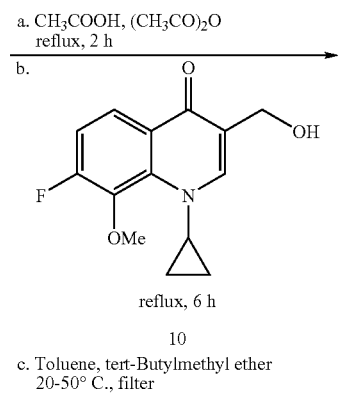

reflux, 6 h

10 c. Toluene, tert-Butylmethyl ether
20-50° C., filter

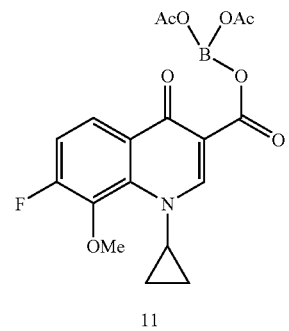

11

A reactor was charged with boron oxide (2.0 kg, 29 mol), glacial acetic acid (8.1 L, 142 mol), and acetic anhydride (16.2 L, 171 mol). The resulting mixture was refluxed at least 2 hours, and then cooled to 40° C., at which temperature, 7-fluoroquinolone acid compound 10 (14.2 kg, 51 mol) was added. The mixture was refluxed for at least 6 hours, and then cooled to about 90° C. Toluene (45 L) was added to the reaction. At 50° C., tert-butylmethyl ether (19 L) was added to introduce precipitation. The mixture was then cooled to 20° C. and filtered to isolate the precipitation. The isolated solid was then washed with tert-butylmethyl ether (26 L) prior to drying in a vacuum oven at 40° C. (50 torr) to afford Compound 11 in a yield of 86.4%.

Raman (cm$^{-1}$): 3084.7, 3022.3, 2930.8, 1709.2, 1620.8, 1548.5, 1468.0, 1397.7, 1368.3, 1338.5, 1201.5, 955.3, 653.9, 580.7, 552.8, 384.0, 305.8. NMR ($CDCl_3$, 300 MHz) δ (ppm): 9.22 (s, 1H), 8.38-8.33 (m, 1H), 7.54 (t, J=9.8 Hz, 1H), 4.38-4.35 (m, 1H), 4.13 (s, 3H), 2.04 (s, 6H), 1.42-1.38 (m, 2H), 1.34-1.29 (m, 2H). TLC (Whatman MKC18F Silica, 60 Å, 200 μm), Mobile Phase: 1:1 (v/v) $CH_3CN$: 0.5N NaCl (aq), UV (254/366 nm) visualization; $R_f$=0.4-0.5.

(D) Synthesis of malate salt of (3S,5S)-7-[3-amino-5-methyl-piperidinyl]-1-cyclopropyl-1,4-dihydro-8-methoxy-4-oxo-3-quinolinecarboxylic acid (Compound 1)

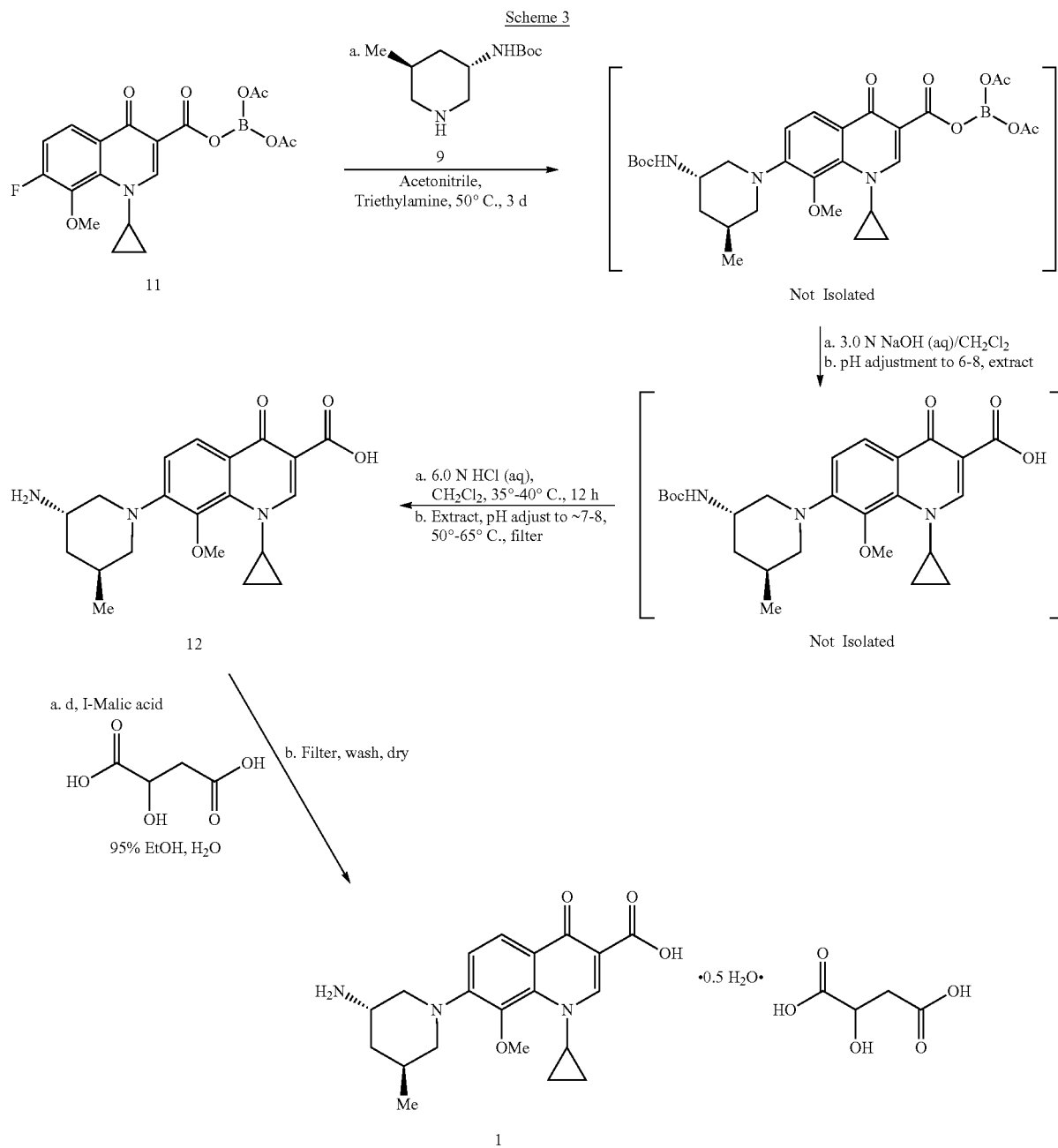

A reactor was charged with Compound 11 (4.4 kg, 10.9 mol), Compound 9 (2.1 kg, 9.8 mol), triethylamine (TEA) (2.1 L, 14.8 mol), and acetonitrile (33.5 L, 15.7 L/kg). The resulting mixture was stirred at approximately 50° C. till completion of the reaction, as monitored by HPLC or reverse phase TLC. It was cooled to approximately 35° C. and the reaction volume was reduced to approximately half by distillation of acetonitrile under vacuum between 0-400 torr. After 28.2 kg of 3.0 N NaOH (aq) solution was added, the reaction mixture was warmed to approximately 40° C., distilled under vacuum until no further distillates were observed, and hydrolyzed at room temperature. Upon completion of hydrolysis, which was monitored by HPLC or reverse phase TLC, 4-5 kg of glacial acetic acid was added to neutralize the reaction mixture.

The resulting solution was extracted 3 times with 12.7 kg (9.6 L) of dichloromethane. The organic layers were combined and transferred to another reactor. The reaction volume was reduced to approximately an half by evaporation at 40° C. After 20.2 Kg 6.0N HCl (aq) solution was added, the reaction mixture was stirred for at least 12 hours at 35° C. After the reaction was completed as monitored by HPLC or reverse phase TLC, agitation was discontinued to allow phase separation. The organic phase was removed and the aqueous layer was extracted with 12.7 kg (9.6 L) of dichloromethane. The aqueous layer was diluted with 18.3 kg distilled water and warmed to approximately 50° C. Dichloromethane was further removed by distillation under vacuum (100-400 torr).

The pH of the aqueous solution was then adjusted to 7.8-8.1 by adding about 9.42 kg of 3.0 N NaOH (aq) below 65° C. The reaction mixture was stirred at 50° C. for at least an hour and then cooled to room temperature. The precipitate was isolated by suction filtration, washed twice with 5.2 kg of distilled water, and dried with suction for at least 12 hours and then in a convection oven at 55° C. for additional 12 hours. Compound 12 (3.2 kg, 79%) was obtained as a solid.

A reactor was charged with 3.2 kg of Compound 12 and 25.6 kg of 95% ethanol. To the reactor was added 1.1 kg of solid D,L-malic acid. The mixture was refluxed temperature (~80° C.). Distilled water (~5.7 L) was added to dissolve the precipice and 0.2 kg of activated charcoal was added. The reaction mixture was passed through a filter. The clear filtrate was cooled to 45° C. and allowed to sit for at least 2 hours to allow crystallization. After the reaction mixture was further cooled to 5° C., the precipitate was isolated by suction filtration, washed with 6.6 kg of 95% ethanol, and dried with suction for at least 4 hours. The solid was further dried in a convection oven at 45° C. for at least 12 hours to afford 3.1 kg of Compound 1 (yield: 70%).

NMR (D$_2$O, 300 MHz) δ (ppm): 8.54 (s, 1H), 7.37 (d, J=9.0 Hz, 1H), 7.05 (d, J=9.0 Hz, 1H), 4.23-4.18 (m, 1H), 4.10-3.89 (m, 1H), 3.66 (br s, 1H), 3.58 (s, 3H), 3.45 (d, J=9.0 Hz, 1H), 3.34 (d, J=9.3 Hz, 1H), 3.16 (d, J=12.9 Hz, 1H), 2.65 (dd, J=16.1, 4.1 Hz, 1H), 2.64-2.53 (m, 1H), 2.46 (dd, J=16.1, 8.0 Hz, 1H), 2.06 (br s, 1H), 1.87 (d, J=14.4 Hz, 1H), 1.58-1.45 (m, 1H), 1.15-0.95 (m, 2H), 0.91 (d, J=6.3 Hz, 3H), 0.85-0.78 (m, 2H).

Compound 1 was dissolved in acetonitrile/water/formic acid (12:88:0.2). The resulting solution was analyzed by gradient reversed phase HPLC with UV detection at 292 nm. The separation was accomplished using gradient elution (see the table) with a mobile phase containing acetonitrile, water, and formic acid on a C8 column (Waters Symmetry Shield RP 8, 5 μm, 4.6×150 mm) at a flow rate of 1.5 mL/min and at 30° C. The compositions of the mobile phase over time are shown in the table below:

| Time (min) | Mobile Phase solution A (0.2% formic acid in water) (%) | Mobile Phase solution B (0.2% formic acid in acetonitrile) (%) |
| --- | --- | --- |
| 0 | 88 | 12 |
| 9.0 | 88 | 12 |
| 22.0 | 30 | 70 |
| 22.5 | 30 | 70 |
| 22.6 | 88 | 12 |
| 30.0 | 88 | 12 |

EXAMPLE 2

Dextrose and sodium chloride formulations were prepared and studied:

1. Formulation in a 5% Dextrose Solution

Compound 1 was dissolved in a 5% dextrose aqueous sterile solution (5 mg/mL). The solution was filtered and transferred to in 100-mL polypropylene bottles. The bottles were capped, sealed, sterilized at 110° C. for 35 min, and stored at 60° C. oven. The solution in the bottles was analyzed on days 0, 5, and 10. The results, shown below, indicate that, for the 5% dextrose solution of compound 1, the active content decreased, the pH value increased, the solution color changed, and brown precipitate formed.

| | Days at 60° C. | | | |
| --- | --- | --- | --- | --- |
| | 0 day | | | |
| | Before Sterilization | After Sterilization | 5 days | 10 days |
| pH | 3.89 | 3.88 | 4.03 | 4.08 |
| Appearance | Clear yellow solution | Clear yellow solution | Dark yellow solution | Brown precipitate |
| Comparative content of Compound 1 (%) | 100.4 | 97.8 | 96.0 | 94.2 |

2. Formulation in a 0.9% Saline Solution

Compound 1 was dissolved in 0.9% saline (5 mg/mL). The solution was filtered and transferred to 100-mL polypropylene bottles. The bottles were capped, sealed, sterilized at 110° C. for 35 min, and stored at 60° C. oven. The solution in the bottles was analyzed on days 0, 5, and 10. The results, shown below, indicate that the formulation was unexpectedly more stable. More specifically, the appearance and pH value remained the same at 60° C. for 10 days. The content of compound 1 increased slightly over time due to water evaporation through the plastic walls of the bottles. The total impurity only slightly increased after 10 days.

| | Time at 60° C. | | |
| --- | --- | --- | --- |
| | 0 day | 5 days | 10 days |
| pH Value | 3.90 | 3.88 | 3.88 |
| Appearance | Clear yellow solution | Clear yellow solution | Clear yellow solution |
| Comparative content of Compound 1 (%) | 102.6 | 103.2 | 104.0 |
| Total Impurity (%) | 0.378 | 0.375 | 0.410 |

Solutions of Compound 1 in 0.9% saline were prepared at the concentrations 0.1, 1, 3, 4, 5, 6, 10 and 15 mg/mL. These solutions were filtered and filled in 100-mL polypropylene bottles. The bottles were capped, sealed, and sterilized at 110° C. for 35 min. Bottles at the concentration of 1, 3, 5, 10 mg/mL were used for a GLP toxicology study on rats and dogs.

EXAMPLE 3

Effects of charcoal, pH values, and iron contents on the formulation were studied:

1. Effect of Charcoal 13.85 g of Compound 1 and 18 g of NaCl were dissolved in sterile water. The final volume of the solution was brought up to 2000 mL by adding additional sterile water with stirring to obtain a solution containing 5 mg/mL Compound 1. The solution was divided into four 500 mL portions. To each of the four portions was added 0%, 0.02%, 0.05% and 0.5% (g/mL) of activated charcoal. The resulting mixtures were boiled with stirring for 25 min and filtered through a 0.45-micron filter paper. The filtrate was added to a series of 100-mL polypropylene bottles, which were capped, sealed, and sterilized at 110° C. for 35 min. Content of Compound 1 and pH for each of the four bottles were analyzed and shown below. 0.05% (g/mL) of activated charcoal was chosen for the formulation process.

| Entry | pH value | Comparative content of Compound 1 (%) | Activated charcoal added |
|---|---|---|---|
| 1 | 3.96 | 109.0 | 0 |
| 2 | 3.88 | 108.8 | 0.02% |
| 3 | 3.88 | 109.2 | 0.05% |
| 4 | 3.80 | 63.9 | 0.5% |

2. Effect of pH 2000 mL solution of Compound 1 in 0.9% saline was prepared in the same manner as described above. The solution was equally divided into 6 portions. The pH values for the 6 portions were adjusted to 2.43, 3.00, 3.76, 4.51, 6.01 and 7.13 by adding dilute hydrochloric acid or sodium hydroxide. The appearance and content of solutions were analyzed and shown below. The results show that Compound 1 at 5 mg/mL in a saline solution precipitated at pH 6.6.

| Entry | Comparative content of Compound 1 (%) | pH Value | Appearance |
|---|---|---|---|
| 1 | 96.68 | 2.17 | clear yellow solution |
| 2 | 94.87 | 3.00 | clear yellow solution |
| 3 | 103.62 | 3.76 (no acid/base added) | clear yellow solution |
| 4 | 101.14 | 4.50 | clear yellow solution |
| 5 | 99.63 | 6.01 | clear yellow solution |
| 6 | N/A | 6.60 | White precipitate |

3. Effect of Iron Content 1000 mL solution of Compound 1 in 0.9% saline was prepared in the same manner as described above. The solution was equally divided into 2 portions. To one portion was added 0.25 g activated charcoal and to the other was added 0.25 g activated charcoal and 0.1 g of iron powder. Each of the resulting mixture was stirred and filtered to a 100-mL polypropylene bottle. The filled bottles were capped, sealed, and sterilized at 110° C. for 35 min. The pH and appearance for each of the solutions are shown below. Based on the results, the process for a parenteral formulation should avoid iron contact.

| Entry | Additive | pH | Appearance |
|---|---|---|---|
| 1 | Iron powder | 3.77 | Reddish Brown |
| 2 | No iron powder | 3.78 | Light yellow |

4. Effect of Temperature and Time During Sterilization 3000 mL solution of solution of Compound 1 in 0.9% saline was prepared in the same manner as described above. To the solution was added 1.5 g of activated charcoal (0.05% g/mL). The mixture was stirred for 15 min and filtered. The filtrate was added to a serious of 100-mL polypropylene bottles. The filled bottles were capped, sealed, and divided into four groups (7 bottles/group). Sterilization of samples was performed at 115° C./35 min, 110° C./35 min, 105° C./35 min. The contents and impurity levels of Compound 1 as well as pH for each group (including a control group) were measured and are shown below. Based on the study, the sterilization of parenteral formulation is chosen at 110° C. for 35 min.

| Entry (Group) | Sterile Temperature | pH Value | Content (%) | Total Impurity (%) |
|---|---|---|---|---|
| 1 | 115° C. | 3.85 | 95.98 | 0.509 |
| 2 | 110° C. | 3.86 | 95.86 | 0.240 |
| 3 | 105° C. | 3.86 | 96.44 | 0.198 |
| 4 | N/A | 3.86 | 95.20 | 0.167 |

5. Effect of Lower Temperature (−15° C.)

Bottles containing 5 mg/mL Compound 1 in 0.9% saline were stored at a −15° C. freezer. Samples were analyzed at days 0, 5 and 10. The results, shown below, indicate that appearance, the compound content, pH and total impurity maintained the same at −15° C. for 10 days.

| | Time at −15° C. | | |
|---|---|---|---|
| | 0 day | 5 days | 10 days |
| Appearance | Clear yellow solution | Clear yellow solution | Clear yellow solution |
| Content | 102.6 | 102.8 | 103.5 |
| pH Value | 3.90 | 3.89 | 3.89 |
| Total Impurity (%) | 0.378 | 0.370 | 0.373 |

6. Effect of Light to Formulation

Bottles containing a solution of Compound 1 (5 mg/mL based on the free base) in 0.9% saline were placed in a light box under 4500Lx+/−500Lx. Samples were analyzed at days 0, 5, and 10. The results, shown below, indicate that there were no changes under intense light.

| | Time under Intense Light | | |
|---|---|---|---|
| | 0 day | 5 days | 10 days |
| Appearance | Clear yellow solution | Clear yellow solution | Clear yellow solution |
| UV Absorption | Consist with Standard | Consist with Standard | Consist with Standard |
| Particulate Matter | Consist with Standard | Consist with Standard | Consist with Standard |
| pH Value | 3.90 | 3.89 | 3.89 |

EXAMPLE 4

A solutions of Compound 1 (5 mg/mL based on the free base) in 0.9% saline was prepared, filtered and transferred to 100-mL polypropylene bottles. The bottles were capped, sealed, sterilized at 110° C. for 35 min, and stored at 40° C. and under 20% relative humidity (RH) for 6 months and 25° C. and under 60% RH for 12 months and tested as shown in the table below.

|  | Intervals (Months) | | | | | | |
| --- | --- | --- | --- | --- | --- | --- | --- |
| Condition | 0 | 1 | 2 | 3 | 6 | 9 | 12 |
| 25° C./60% RH | X | X | X | X | X | | |
| 40° C./20% RH | X | | | X | X | X | X |

At each sampling point (marked as "X" in the above table), samples were evaluated for their appearance, color, clarity, pH, UV absorption, assay and impurity. No significant changes were observed.

EXAMPLE 5

In vitro and in vivo activities of Compound 1 were studied as follows:

1. In Vitro Antibacterial Activity

Various bacterial species, such as Gram positive bacteria (e.g., *Clostridium, Staphylococcus* and *Streptococcus*), Gram negative bacteria (e.g., *Moraxella, Haemophilus, Pseudomonas, Proteus*, and *Bacteriodes*), anaerobic and atypical pathogens, were isolated from clinical samples. The antibacterial activity of Compound of Formula I against these bacterial species were determined using agar dilution assays described in the U.S. National Committee for Clinical Laboratory, M7-A6, 2003, and M11-A5, 2001.

The results show that Compound 1, had potent, broad-spectrum antibacterial activity, including activity against Gram positive, Gram negative, anaerobic, and atypical pathogens. The salt was especially active against staphylococci and streptococci, including methicillin-resistant *S. aureus* (MRSA) and multi-resistant *S. pneumoniae*. Against ciprofloxacin-sensitive methicillin-susceptible *S. aureus* (MSSA) and MRSA, the minimum inhibitory concentration for 90% ($MIC_{90}$) of the isolates tested was 0.06 μg/mL. The $MIC_{90}$ was 0.5 μg/mL against ciprofloxacin-resistant MSSA and 1 μg/mL against ciprofloxacin-resistant MRSA. Against susceptible, penicillin-resistant, and macrolide-resistant *S. pneumoniae*, the $MIC_{90}$ was 0.12 μg/mL. In this study, the MIC values against all staphylococci and streptococci were <2 μg/mL and <1 μg/mL, respectively. Considering all Gram positive organisms, Compound 1 was 4- to 8-fold more potent than levofloxacin and 2- to 4-fold more potent than gatifloxacin.

Among Gram negative organisms, Compound 1 was active against *Moraxella catarrhalis* ($MIC_{90}$=0.03 μg/mL), *Haemophilus influenzae* ($MIC_{90}$=0.12 μg/mL), and *Neisseria gonorrhoeae* ($MIC_{90}$=0.06 μg/mL). The compound was active against most enteric organisms, with $MIC_{90}$=0.12 μg/mL for *E. coli*, $MIC_{90}$=1 μg/mL for *Klebsiella pneumoniae* and $MIC_{90}$=0.5 μg/mL for *Proteus mirabilis*. It was also active against many isolates of *Pseudomonas aeruginosa* as well as anaerobic pathogens, *Clostridium difficile* and *Bacteroides* species.

2. In Vivo Efficacy

The in vivo antibacterial efficacy of Compound 1 was evaluated in a mouse model. Mice were anesthetized and infected intranasally with a lethal amount of *S. pneumoniae* Stp 6301. Twelve, eighteen, and twenty-four hours after the infection, a composition containing Compound 1 or moxifloxacin (as a positive control), 0.7% lactic acid, and 3% dextrose was administered subcutaneously to the mice at a total dose of 50, 25, 12.5, or 6.25 mg/kg. Half of the treated mice were euthanized four hours after the last treatment of Compound 1 or moxifloxacin and their blood and lung tissues were collected. The number of viable bacteria in the blood and lung tissues was then determined. The lung tissues were also subjected to histopathologic evaluation. The other half of the mice were monitored for 6 days and the number of the surviving mice was recorded.

The results show that Compound 1 significantly reduced viable bacteria in lung and blood at all tested dosage levels, compared to vehicle-treated controls. In addition, the antibiotic provided complete protection from lethal infection (100% survival) at all tested dosage levels. At the same dosage levels, Compound 1 was more efficacious than moxifloxacin in this pulmonary infection model.

OTHER EMBODIMENTS

All of the features disclosed in this specification may be combined in any combination. An alternative feature serving the same, equivalent, or similar purpose may replace each feature disclosed in this specification. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A method of treating an infectious disease, comprising administering via parenteral injection or infusion to a subject in need thereof an effective amount of a formulation containing:

D,L-malate salt of the compound of formula I:

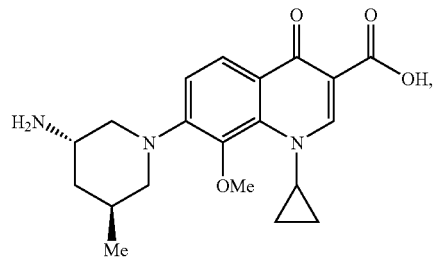

Formula I water, and an isotonic agent at a concentration of 0.2% to 13% w/v, wherein the compound and isotonic agent are dissolved in the water and the infectious disease is infection with Gram positive bacteria.

2. The method of claim 1, wherein the infectious disease is infection with methicillin-resistant *S. aureus* or multi-resistant *S. pneumoniae*.

3. The method of claim 1, wherein the isotonic agent is sodium chloride.

4. The method of claim 3, wherein the concentration of the compound in the formulation is 0.2 to 45 mM and the concentration of sodium chloride in the formulation is 0.2 to 1.3% v/w.

5. The method of claim 4, wherein the formulation is administered via intravenous injection or infusion.

6. The method of claim 5, wherein the sodium chloride concentration in the formulation is 0.9% w/v.

7. The method of claim 5, wherein the infectious disease is infection with methicillin-resistant *S. aureus* or multi-resistant *S. pneumoniae*.

8. The method of claim 5, wherein the formulation further comprises a stabilizing agent, the stabilizing agent being selected from the group consisting of histidine, lysine, glycine, sucrose, fructose, trehalose, and a mixture thereof.

9. The method of claim 5, wherein the formulation further comprises a buffer, the buffer being selected from the group consisting of acetate, citrate, tartarate, lactate, succinate, malate, or phosphate.

10. The method of claim 5, wherein the formulation further comprises an antioxidant, the antioxidant being selected from the group consisting of sodium bisulfite, butylated hydroxy anisole, cysteine, gentisic acid, monosodium glutamate, sodium thioglycolate, and ascorbic acid.

11. The method of claim 1, wherein the formulation further comprises a stabilizing agent at a concentration of 0.1-1.0% w/v and a buffer at a concentration of 0.01-5% w/v.

12. The method of claim 1, wherein the isotonic agent is selected from the group consisting of glycerine, lactose, mannitol, dextrose, sodium sulfate, and sorbitol.

13. The method of claim 12, wherein the isotonic agent is dextrose and its concentration in the formulation is 1-7% w/v.

14. The method of claim 13, wherein the formulation further comprises a stabilizing agent at a concentration of 0.1-1.0% w/v and a buffer at a concentration of 0.01-5% w/v.

15. The method of claim 13, wherein the formulation is administered via intravenous injection or infusion.

16. The method of claim 1, wherein the isotonic agent is sodium chloride and its concentration in the formulation is 0.2-1.3% w/v.

17. A method of treating an infectious disease, comprising administering via parenteral injection or infusion to a subject in need thereof an effective amount of a formulation containing:

D,L-malate salt of the compound of formula I:

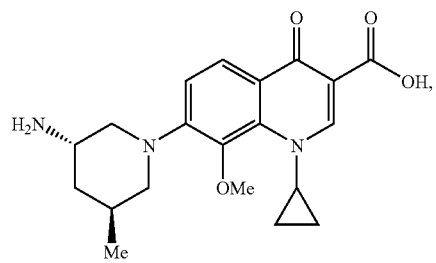

Formula I water, and
an isotonic agent at a concentration of 0.2% to 13% w/v,
    wherein the compound and isotonic agent are dissolved in the water and the infectious disorder is infection with anaerobic bacteria.

18. The method of claim 17, wherein the isotonic agent is sodium chloride.

19. The method of claim 18, wherein the concentration of the compound in the formulation is 0.2 to 45 mM and the concentration of sodium chloride in the formulation is 0.2 to 1.3% v/w.

20. The method of claim 17, wherein the formulation further comprises a stabilizing agent, the stabilizing agent being selected from the group consisting of histidine, lysine, glycine, sucrose, fructose, trehalose, and a mixture thereof.

21. The method of claim 17, wherein the formulation further comprises a buffer, the buffer being selected from the group consisting of acetate, citrate, tartarate, lactate, succinate, malate, or phosphate.

22. The method of claim 17, wherein the formulation further comprises an antioxidant, the antioxidant being selected from the group consisting of sodium bisulfate, butylated hydroxy anisole, cysteine, gentisic acid, monosodium glutamate, sodium thioglycolate, and ascorbic acid.

23. The method of claim 17, wherein the isotonic agent is selected from the group consisting of glycerine, lactose, mannitol, dextrose, sodium sulfate, and sorbitol.

24. The method of claim 23, wherein the isotonic agent is dextrose and its concentration in the formulation is 1-7% w/v.

25. The method of claim 24, wherein the formulation further comprises a stabilizing agent at a concentration of 0.1-1.0% w/v and a buffer at a concentration of 0.01-5% w/v.

26. The method of claim 24, wherein the formulation is administered via intravenous injection or infusion.

27. The method of claim 17, wherein the isotonic agent is sodium chloride and its concentration in the formulation is 0.2-1.3% w/v.

* * * * *